United States Patent [19]

Poindexter et al.

[11] Patent Number: 4,755,512
[45] Date of Patent: Jul. 5, 1988

[54] PHARMACEUTICALLY USEFUL DIHYDROPYRIDINYLDICARBOXYLATE AMIDES AND ESTERS INCORPORATING ARYLPIPERAZINYLALKYL MOITIES

[75] Inventors: Graham Poindexter; Davis L. Temple, Jr., both of Evansville, Ind.

[73] Assignee: Bristol-Myers Company, New York, N.Y.

[21] Appl. No.: 693,426

[22] Filed: Jan. 22, 1985

Related U.S. Application Data

[63] Continuation-in-part of Ser. No. 599,097, Apr. 11, 1984, abandoned.

[51] Int. Cl.[4] .................. A61K 31/44; A61K 31/495; C07D 401/12; C07D 401/14
[52] U.S. Cl. .................................... 514/252; 514/253; 544/295; 544/296; 544/357; 544/364; 544/365; 546/321
[58] Field of Search ............... 544/295, 296, 357, 364, 544/365; 514/252, 253

[56] References Cited

U.S. PATENT DOCUMENTS

| | | | |
|---|---|---|---|
| 3,485,847 | 12/1969 | Bossert et al. | 546/321 |
| 3,821,225 | 6/1974 | Regnier et al. | 544/364 |
| 3,905,970 | 9/1975 | Bossert et al. | 544/365 |
| 3,974,275 | 8/1976 | Bossert et al. | 546/281 |
| 3,996,234 | 12/1976 | Bossert et al. | 544/365 |
| 4,393,070 | 7/1983 | Sato et al. | 546/286 |

FOREIGN PATENT DOCUMENTS

| | | |
|---|---|---|
| 60674 | 8/1982 | European Pat. Off. |
| 63365 | 10/1982 | European Pat. Off. |
| 88903 | 9/1983 | European Pat. Off. |
| 94159 | 11/1983 | European Pat Off. ............. 544/364 |
| 97821 | 1/1984 | European Pat. Off. |

OTHER PUBLICATIONS

Bossert, et al., "4-Aryldihydropyridines, a New Class of Highly Active Calcium Antagonists", Angew. Chem., Int. Ed. Engl. 20, (1981) pp. 762–769.

Schramm, et al., "Novel Dihydropyridines with Positive Inotropic Action Through Activation of $CA^{2+}$ Channels", Nature, 30 (Jun. 9, 1983), pp. 535–537.

Aritomi, et al., Chem. Pharm. Bull., 29 (11) 3163–6171 (1980).

Primary Examiner—Glennon H. Hollrah
Assistant Examiner—James H. Turnipseed
Attorney, Agent, or Firm—Robert H. Uloth

[57] ABSTRACT

A series of 1,4-dihydropyridin-3,5-yl dicarboxylic acid amides and esters incorporating an arylpiperazinylalkyl moiety have been prepared possessing the general formula

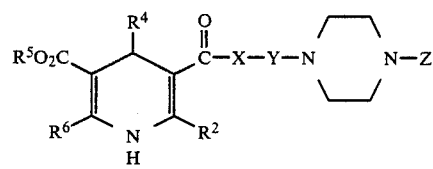

wherein $R^4$ is cycloalkyl, aryl or hetaryl, generally with electronwithdrawing substituents; $R^2$ and $R^6$ are lower alkyl, alkanol, alkoxyalkyl, or alkylaminoalkyl; $R^5$ is $R^2$ or arylpiperazinylalkyl; X is O or NH; Y is lower alkylene, alkoxyalkylene, alkylaminoalkylene; and Z is phenyl, substituted phenyl, pyridinyl, substituted pyridinyl, or pyrimidinyl. Compounds of this series demonstrate activity as calcium and alphaadrenergic blockers in in vitro testing and antihypertensive, antiischemic, and platelet function inhibiting actions in in vivo screens.

9 Claims, No Drawings

PHARMACEUTICALLY USEFUL DIHYDROPYRIDINYLDICARBOXYLATE AMIDES AND ESTERS INCORPORATING ARYLPIPERAZINYLALKYL MOITIES

CROSS-REFERENCE TO RELATED APPLICATION

This is a continuation-in-part application of Ser. No. 599,097 filed Apr. 11, 1984 now abandoned.

BACKGROUND OF THE INVENTION

The present invention concerns the heterocyclic carbon compounds of the 1,4-dihydropyridine class with a 3-carboxylate or carboxamido group linked to an aryl-piperazinylalkylene moiety. These compounds possess bio-affecting properties.

A substantial body of prior art has evolved over the last decade involving compounds of 4-aryl-1,4-dihydropyridine series which have calcium antagonist properties and are useful in the treatment of cardiovascular diseases. These calcium blocking effects appear to mediate vasodilation making these compounds useful in treating angina and hypertension. These structures are typified by nifedipine. (Formula 1);

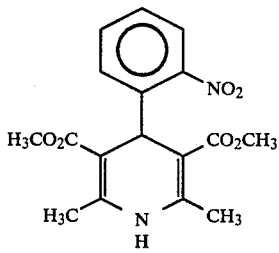

chemically 4-(2'-nitrophenyl)-2,6-dimethyl-3,5-dicarbomethoxy-1,4-dihydropyridine. Nifedipine and some related 4-aryl-1,4-dihydropyridines are the subject of U.S. Pat. No. 3,485,847 issued Dec. 23, 1969. Numerous subsequent patent have been granted covering 1,4-dihydropyridines in which other substituent groups have been incorporated at the various ring positions of the dihydropyridine moiety via a diversity of chemical bonding groups.

Utilizing medicinal chemical techniques, an object of the instant invention was to design a therapeutic agent combining $\alpha_1$-adrenergic blocking properties with the calcium blocking action in a single molecular structure. The biological rationale for the combination of actions suggests that such an agent would provide potent and efficacious treatment for vasospastic circulatory disorders.

Art related to the series of compounds of the present invention may be generalized by the following structural formula (2):

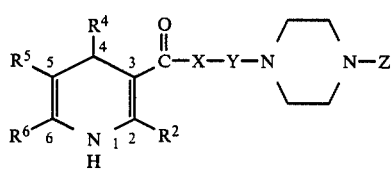

wherein $R^2$, $R^4$, $R^5$ and $R^6$ could be any of a number of substituent groups which have been defined previously in the voluminous dihydropyridine literature; but with specific attention being given the definition for the substituent structure attached to the 3-position of the 1,4-dihydropyridine ring. To our knowledge, no aryl- or hetaryl-piperazinylalkyl moiety has been incorporated heretofore in a 1,4-dihydropyridine ring compound via a carboxylate amide or ester functionality in the 3-position of the ring. The most relevant art to be disclosed is, in our judgment, the divisional patents, U.S. Pat. No. 3,905,970 and U.S. Pat. No. 3,974,275 issued to Bossert, et al., on Sept. 16, 1975, and Aug. 10, 1976, respectively. The compounds disclosed and claimed in these patents have as the 3-substituent side chain moiety

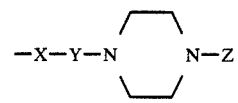

shown in structure (2) above, the following (2a):

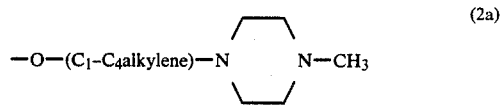

This same 3-substituent side chain (2a) was also disclosed in U.S. Pat. No. 4,393,070 issued to Sato, et al., on July, 1983.

European Patent Application No. 88,903, published Sept. 21, 1983 discloses 1,4-dihydropyridine art with the ester group of the 3-carboxylate moiety having the following structure (2b):

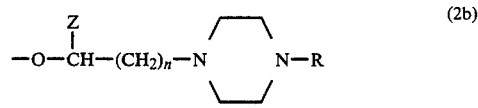

wherein n is 0 to 5; Z is aryl or hetaryl; and R is lower alkyl, alkoxycarbonyl, or alkanoylamino. The point of novelty disclosed for these antihypertensive agents is based on Z, in that "... the introduction of the aromatic ring or aromatic heterocyclic ring at alpha-position of the cyclic amino alkyl ester moiety in the side chain causes increased and remarkably prolonged effectiveness."

Somewhat less related, European Patent Application No. 63,365, published Oct. 27, 1982 discloses 1,4-dihydropyridines with a 3-carboxylate ester group comprising a piperidine ring (3):

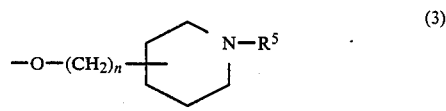

wherein n is 0 to 3, and $R^5$ is arylalkyl or acyl.

Additionally, there are 1,4-dihydropyridine compounds disclosed which have an arylpiperazine system attached by an alkyl or alkoxyalkyl chain to the 2-position of the dihydropyridine ring. Aritomi, et al., in *Chem. Pharm. Bull.* 29 (11), 3163-71 (1980) disclose compounds having the (4) group in ring position 2:

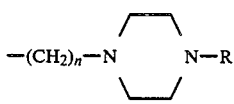

(4)

wherein n=2 and R is alkyl, aryl, or arylalkyl. Specifically disclosed, as an example, is compound (4a).

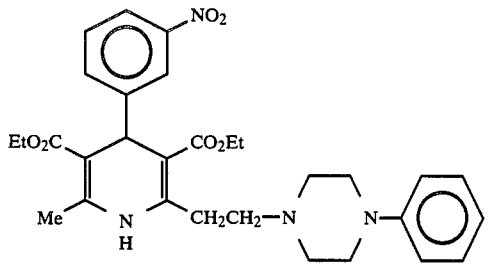

(4a)

European Patent Application No. 60,674, published Sept. 22, 1982 discloses anti-ischemic and antihypertensive agents of structure (5)

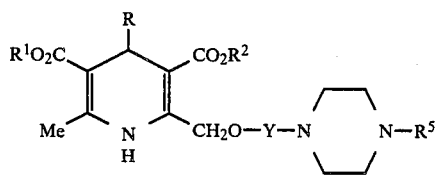

(5)

wherein Y is an ethylene or propylene chain; and $R^5$ is $C_{1-4}$ alkyl, aryl, arylalkyl, and the like. These compounds are easily distinguished structurally from the compounds of the instant invention by virtue of ring position and the linking functional group. That is, compounds of the instant invention contain an α-blocking aryl- or hetaryl piperazine moiety linked by an alkyl, alkoxyalkyl, or alkylaminoalkyl chain to a carboxylate or carboxamide function in ring position 3.

All of the above mentioned compounds derive their therapeutic usefulness, according to prevailing theory of their biological mechanism, due to their inate ability to act as calcium channel blockers. In essence, the instant compounds may be distinguished over compounds of the prior art both on the basis of molecular structure and also by biological action. The instant compounds possess both calcium channel and alpha-adrenergic blocking properties, thereby enhancing the usefulness of these compounds in treating hypertension and ischemic disorders. The instant compounds have also been found to possess useful actions in inhibiting certain functions of blood platelets. There is nothing in the prior art which anticipates or suggests the compounds of the present invention.

SUMMARY AND DETAILED DESCRIPTION OF THE INVENTION

The present invention includes the compounds of Formula I

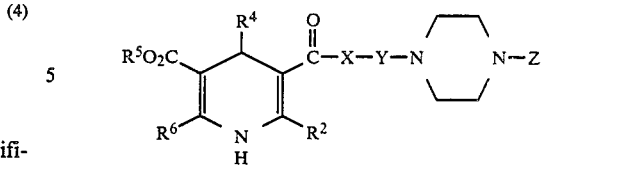

I and the acid addition salts of these substances. In the foregoing structural formula the symbols $R^2$, $R^4$, $R^5$, $R^6$, X, Y, and Z have the following meanings. $R^2$ and $R^6$ are independently selected from lower alkyl, hydroxyalkyl, alkoxyalkyl, alkylaminoalkyl, or dialkylaminoalkyl and may be the same or different. Lower alkyl means $C_1$ to $C_4$; alkoxyalkyl refers to a $C_1$ to $C_4$ alkylene chain and a $C_1$ to $C_4$ alkyl group connected by an oxygen atom; similarly, the alkylaminoalkyl and dialkylaminoalkyl refer to lower alkyl groups and a $C_1$ to $C_4$ alkylene chain connected by a secondary (—NH—) or tertiary $$\diagdown_{N-)}\diagup$$

amino group. $R^4$ is cycloalkyl of 5 to 7 carbon atoms, bicycloalkenyl of 7 to 9 carbon atoms, hetaryl, such as furanyl, indolyl, methylthiopyridyl, thienyl, benzoxadiazolyl, benzothiadiazolyl, and the like; aryl meaning phenyl, naphthyl, or substituted phenyl, with the substituents comprising acetamino, lower alkyl, lower alkoxy, cyano, halogen, hydroxyl, nitro, trifluoromethyl, trifluoromethylsulfonyl, and methylsulfonyl and the like. $R^5$ is $R^2$ or $$X-Y-N\diagup\diagdown N-Z.$$

X is 0 or NH; Y is a lower ($C_{1-5}$) alkylene chain, alkoxyalkylene, or alkylaminoalkylene chain; and Z is phenyl, pyridinyl, or pyrimidinyl, either unsubstituted or substituted with one or more substituent groups selected from among lower alkyl, lower alkoxy, cyano, halo, and trifluoromethyl.

Preferred compounds of the instant invention have the structure of Formula I wherein $R^2$ and $R^6$ are lower alkyl, $R^4$ is nitrophenyl, $R^5$ is lower alkyl or $$X-Y-N\diagup\diagdown N-Z,$$

X is 0 or NH, Y is a $C_2$ to $C_5$ alkylene chain, and Z is substituted phenyl. The most preferred compounds of the instant invention have the Formula I structure wherein $R^2$ and $R^6$ are methyl, $R^4$ is 2- or 3-nitrophenyl, $R^5$ is methyl or

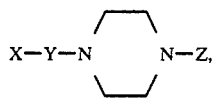

X is O, Y is a propylene chain and Z is a 2-substituted phenyl ring, preferably o-methoxyphenyl.

The compounds of the present invention can exist as optical isomers and both the racemic mixtures of these isomers as well as the individual optical isomers themselves are within the scope of the present invention. The racemic mixtures can be separated into their individual isomers through well known techniques such as the separation of the diastereomeric salts formed with optically active acids, followed by conversion back to the optically active bases.

As indicated, the present invention also pertains to the pharmaceutically acceptable non-toxic salts of these basic compounds. Such salts include those derived from organic and inorganic acids such as, without limitation, hydrochloric acid, hydrobromic acid, phosphoric acid, sulfuric acid, methanesulfonic acid, acetic acid, tartaric acid, lactic acid, succinic acid, citric acid, maleic acid, sorbic acid, aconitic acid, salicylic acid, phthalic acid, embonic acid, enanthic acid, and the like.

The compounds of the present invention may be produced by the following processes which employ variations of the Hantzsch synthetic reaction applied to the appropriate starting materials.

Specifically, the present invention utilizes a modified Hantzsch process for preparation of the compounds of Formula I according to the reaction schemes following hereinbelow. The general reaction process and many of the required intermediate compounds have been previously described in U.S. Pat. No. 4,414,213 which is hereby incorporated herein by reference.

General processes for preparation of:

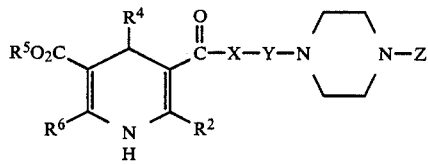

General Scheme:

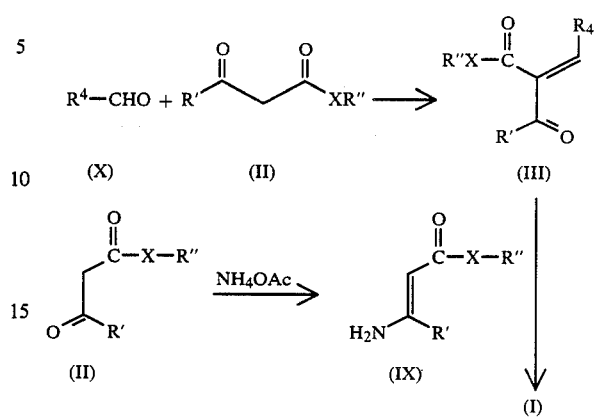

In the foregoing general scheme, $R^4$ and X are as defined in Formula I. R' may be either $R^2$ or $R^6$ of Formula I; R" may be either $R^5$ or

Preparation of the compounds of Formula I according to the process of the general scheme generally comprises heating IX-type and III-type intermediate compounds neat or in the presence of a wide variety of a reaction inert organic solvents. Suitable solvents include but are not limited to benzene, toluene, tetrahydrofuran, dibutylether, butanol, hexanol, methanol, dimethoxyethane, ethyleneglycol, ethanol, propanol, etc. Suitable reaction temperatures are from about 60° to 150° C. No catalyst or condensation agent is usually required. The intermediate enamine esters or amides (IX) are generated by Hantzsch-type reaction conditions (NH4OAc/alcohol) from II intermediates. The IV intermediates are usually not isolated but are allowed to react immediately with III compounds. The intermediate acylcinnamate compounds of structure III are prepared in general by utilizing known Knoevenagel condensation reaction conditions. In general, appropriately substituted aldehydes and 1,3-dicarbonyl compounds were condensed to give III.

Preferred variations of the general scheme are shown in the reaction schemes which follow.

Scheme 1 (X=O)

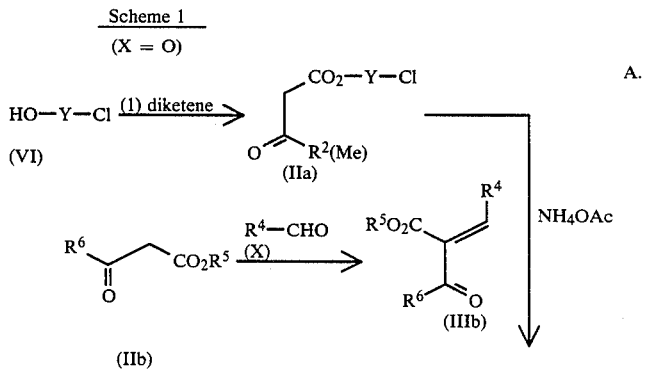

Scheme 1
(X = O)
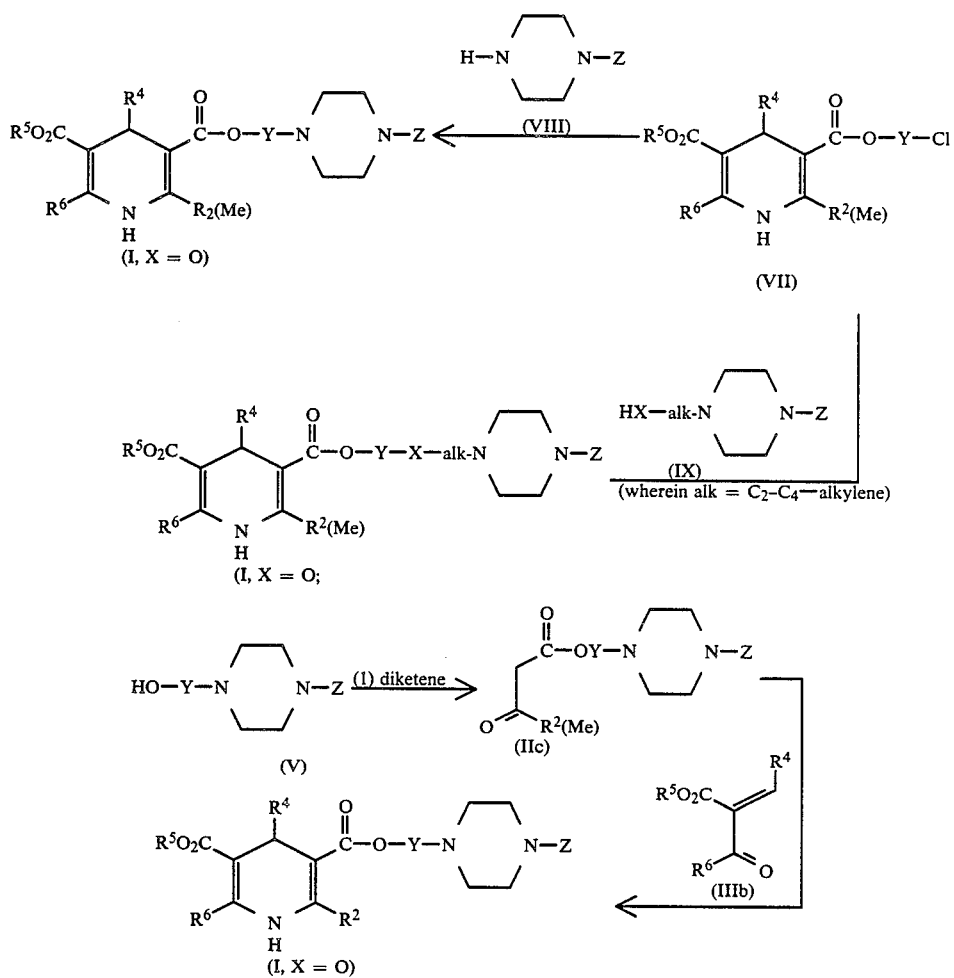
Scheme 2
(X = NH)
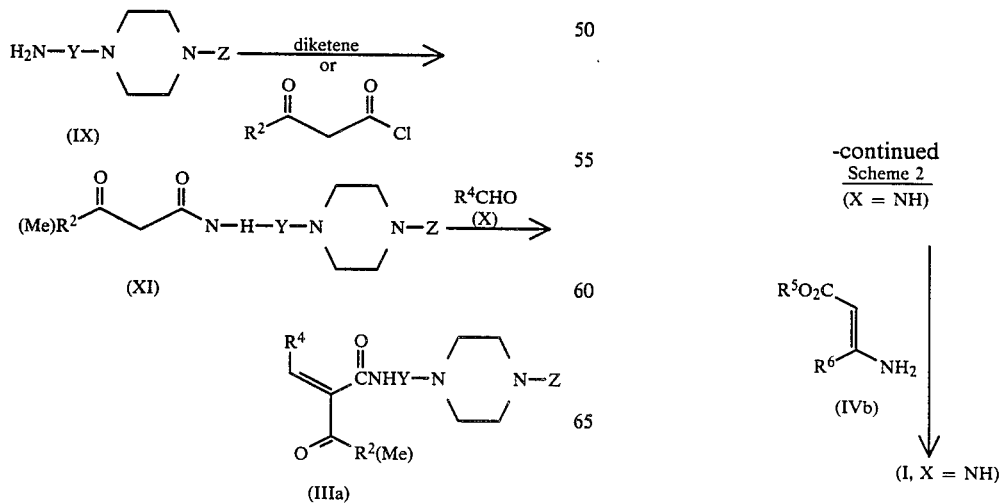

Scheme 3

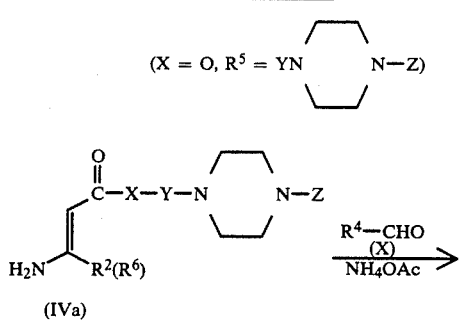

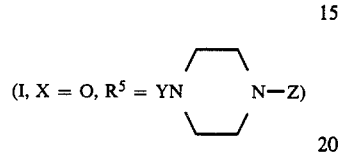

In these foregoing schemes, $R^2$, $R^4$, $R^5$, $R^6$, X, Y, and Z are as defined in Formula I.

According to Scheme 1, an intermediate 1,3-dicarbonyl compound II, generated by treatment of either a chloroalkanol (VI) or arylpiperazinylalkanol (V) with either Maldrum's acid (cf: *The Merck Index*, 10th Edition, 5635, page 828 (1983)) as in Scheme 4, or with diketene is subjected to modified Hantzsch condensation conditions (ammonium acetate/ethanol) followed by reaction with the cinnamate intermediate (IIIa) to afford either a desired product of Formula (I), as in Scheme IB, or the chloroalkyl ester compound (VII) shown in Scheme 1A. The intermediate compound (VII) may be reacted with either a simple arylpiperazine (VIII) or an arylpiperazinylalkyl alcohol or amine (IX) giving different embodiments of 3-carboxylate ester compounds of Formula (I), as shown in Scheme IA. The dihydropyridine products (I) obtained by the methods outlined in Scheme 1 are isolated in moderate yields following chromatography.

Synthetic Scheme 2 illustrates the reaction sequence utilized to obtain the 3-carboxamide subclass of Formula I products. In Scheme 2, an aminoalkylpiperazine (IX; prepared from the corresponding arylpiperazine (VIII) and a chloroalkyl phthalimide via the well-known Gabriel synthesis) is treated with diketene or an appropriate alkanoylacetyl halide to generate the intermediate acetoacid amide (XI) which is converted to the cinnamic acid amide (IIIa) utilizing Knovenagel conditions ($R^4$CHO, piperidine and acetic acid in benzene). Application of the general reaction to the intermediate compounds IIIa and IVb, as shown, yields the desired I product wherein X=NH.

Scheme 3 indicates a route employed for the synthesis of symmetrical dihydropyridines, i.e. the 3- and 5-carboxylate groups are identical. As shown, intermediate compound IVa (prepared from IIc under Hantzsch reaction conditions) undergoes condensation with an appropriate $R^4$CHO to afford the desired I product.

Additional II and XI reaction intermediates utilized in preparation of the compounds comprising the instant invention can be prepared according to the following synthetic schemes or by modifications thereof which would be obvious to practitioners skilled in the chemical art.

Scheme 4
($R^2$ and/or $R^6$ is alkyl)

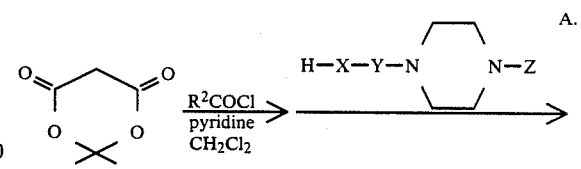

(Meldrum's acid)

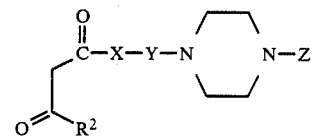

IIa, X = O
XIa, X = NH

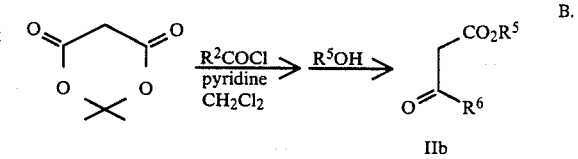

For more details of Scheme 4 cf: Y. Oikawa, et al., *J. Org. Chem*, 43, 2087 (1978).

Scheme 5
($R^2$ and/or $R^6$ is alkyl—X—alkyl)

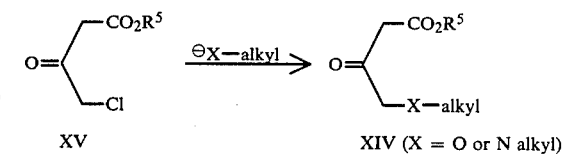

XV     XIV (X = O or N alkyl)

In Scheme 5, $R^5$ could also be

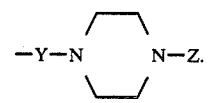

Additionally, if the structural moiety represented by "alkyl" in XIV were a standard O— or N-protecting group in organic synthesis, then its removal would generally give rise to intermediates where $R^2$ or $R^6$ were alkanol or alkylamino as defined hereinabove. In general, XIV is prepared by treating a cold (0°) solution of readily available intermediate XV with lithium diisopropylamide followed by introduction of an alkali metal salt of the X-alkyl reagent. Examples of this reagent would be sodium methoxide, sodium ethoxide, 2-phenylethyl ethoxide, sodium phenoxide, lithium methylamide, lithium dimethylamide, lithium methylphenylamide, and the like. The reaction medium is an inert organic liquid, preferably tetrahydrofuran or tetrahydrofuran-DMSO. Isolation and purification of XIV is achieved by chromatography on silica gel.

The compounds of this invention have been found to possess several useful pharmacological properties. The evaluation of these pharmacological properties was affected by means of both in vitro and in vivo biological screens. In vitro screening included calcium activity in various smooth muscle systems such as rat dorsal aorta, portal vein, and trachea; and α-binding affinities determined in rat heart and brain. In general, the preferred compounds of the instant invention possessed calcium entry blockade activity with potencies approximating the reference compound nifedipine. The α-binding activity was much greater for the instant compounds than for nifedipine with most members of the present series being one or two orders of magnitude more potent.

Dose-shift studies, involving the response to phenylephrine in ganglion-blocked, anesthetized rats, demonstrated that α-adrenoceptor blockade was the pharmacological result of the α-binding. The methodology is described by Deitchman, et al., in *J. Pharmacol. Methods*, 3, 311–321 (1980).

In vivo testing included vasodilating results in the ganglion-blocked, angiotensin-II supported rat and antihypertensive screening in either the spontaneous hypertensive rat (SHR) or DOCA salt rats. In general, vasodilating activity paralleled calcium blocking activity for members of the instant series. The antihypertensive screening data indicated that good calcium and α-adrenergic blocking activity in concert produced the most dramatic antihypertensive effects. A most preferred compound, BMY 20064

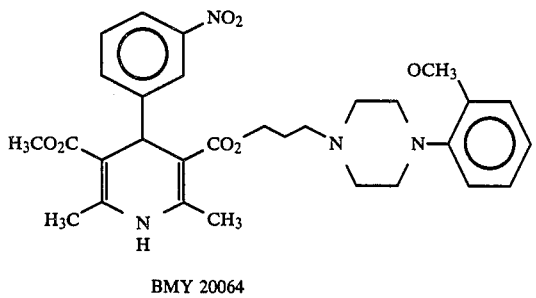

BMY 20064 was administered orally to both normotensive and spontaneously hypertensive conscious rats. Doses of 1 and 10 l mg/kg elicited maximal mean arterial blood pressure reductions of 25 and 53 mmHg, respectively, in the normotensive rat group and 34 and 100 mmHg, respectively, in the spontaneously hypertensive rat group. These mean arterial blood pressure responses observed in both groups were rapid in onset (<10 minutes) and the significantly mean arterial blood pressure persisted for >4 hours after the higher dose of BMY 20064.

Additionally, BMY 20064 and nifedipine were studied in anesthetized beagle dogs to determine their comparative acute hemodynamic effects. The two compounds exhibited similar potency and hemodynamic profiles in this particular hemodynamic model.

The specific tests employed in evaluation of the compounds of the instant invention were carried out according to the following procedures or with slight modification. Demonstration that the instant compounds possess specific blocking action on calcium ion channels resulted from in vitro testing which consisted of suspending guinea pig ileal longitudinal smooth muscle strips in baths containing Tyrodes solution maintained at 37° C. aerated with 95% $O_2$–%5 $CO_2$. The tissues were equilibrated for 60 minutes prior to the start of all experiments. A single response to carbachol is obtained and used in all experiments as a control maximum. In between successive doses, the tissues are re-equilibrated and washed with Tyrodes solution every 15 minutes. To study the effect of the compounds, the tissues are exposed to the antagonist for 10 minutes prior to the addition of carbachol. For all experiments, only one antagonist in any one concentration is tested in any tissue. The results are expressed as molar concentrations of antagonists which inhibit the muscle response by 50%. Since calcium antagonism generally inhibits excitation-contraction coupling in vascular smooth muscle, agents of this type usually evoke vasodilation. Testing of selected compounds of the instant invention in the ganglion-blocked, angiotension II-supported rat model (Deitchman, et al., *J. Pharmacol. Methods*, 3, 311–321 (1980)) demonstrated vasodilation with its concomitant lowering of blood pressure.

Additionally, the selected compounds of the instant invention have been examined in vitro and in vivo in laboratory tests developed to predict a drug's potential to protect cardiac tissue from injury due to ischemia. These tests utilize the known relationship between progressive depletion of high energy phosphate and the onset of lethal cell injury in ischemic myocardium. Results of these screening tests demonstrate that the selected compounds possess potent anti-ischemia action.

Finally, compounds of the instant invention exhibit potent inhibition of various aspects of blood platelet function. These changes are not related to the compounds calcium block action. This is evidenced by Table 1 which displays the comparative effects of BMY 20064 with two reference calcium entry blockers, nifedipine and verapamil.

TABLE 1

| Comparative Effects of Calcium Entry Blockers on Various Aspects of Blood Platelet Function in Platelet Rich Plasma (Rabbit) | | | | |
|---|---|---|---|---|
| Compound | Collagen Aggregation | Activity Shape Change | ($EC_{50}$ in mg/mL) Platelet Release Reaction | Clot Retraction |
| Nifedipine | 176 | >128 | >128 | >128 |
| Verapamil | 151 | 128 | 84 | >128 |
| BMY 20064 | 11 | 12 | 12 | 0.1 |

As can be seen, there is little similarity between the effects of BMY 20064 and the reference compounds on platelet function.

In summary of the foregoing discussion of biological activities, the instant compounds have cardiovascular properties particularly suited to their use in hypertension and ischemia. Thus, another aspect of the instant invention concerns a process for ameliorating either hypertension or ischemia in a mammal in need of such treatment which comprises systemic administration to such mammal of an effective dose of a Formula I compound or a pharmaceutically acceptable acid addition salt thereof. On the basis of animal testing, an effective oral dose could be expected to from about 1 to 20 mg/kg and an effective parenteral dose could be expected to be lower, in the range of about 0.05 to 1 mg/kg body weight.

For clinical applications, however, the dosage and dosage regimen must in each case be carefully adjusted, utilizing sound professional judgment and considering the age, weight and condition of the recipient, the route of administration and the nature and gravity of the illness. Generally the compounds of the instant invention will be administered in the same manner as for the reference drug nifedipine and the daily oral dose will comprise from about 5 to to about 50 mg, preferably 10 to 20 mg administered from 1 to 3 times a day. In some instances, a sufficient therapeutic effect can be obtained at lower doses while in others, larger doses will be required.

The term systemic administration as used herein refers to oral, rectal, and parenteral (i.e. intramuscular, intravenous, and subcutaneous) routes. Generally, it will be found that when a compound of the present invention is administered orally, which is the preferred route, a larger quantity of reactive agent is required to produce the same effect as a smaller quantity given parenterally. In accordance with good clinical practice, it is preferred to administer the instant compounds at a concentration level that will produce effective antihypertensive and/or anti-ischemic effects without causing any harmful or untoward side effects.

Therapeutically, the instant compounds are generally given as pharmaceutical compositions comprised of an effective antihypertensive and/or anti-ischemic amount of a compound of Formula I or a pharmaceutically acceptable acid addition salt thereof and a pharmaceutically acceptable carrier. Pharmaceutical compositions for effecting such treatment will contain a major or minor amount, e.g. from 95 to 0.5% of at least one compound of the present invention in combination with the pharmaceutical carrier, the carrier comprising one or more solid, semi-solid, or liquid diluent, filler, and formulation adjuvant which is non-toxic, inert and pharmaceutically acceptable. Such pharmaceutical compositions are preferably in dosage unit forms; i.e., physically discrete units containing a predetermined amount of the drug corresponding to a fraction or multiple of the dose which is calculated to produce the desired therapeutic response. The dosage units can contain 1, 2, 3, 4, or more single doses, or, alternatively, one-half, one-third, or one-fourth of a single dose. A single dose preferably contains an amount sufficient to produce the desired therapeutic effect upon administration at one application of one or more dosage units according to the pre-determined dosage regimen usually a whole, half, third or quarter of the daily dosage administered once, twice, three, or four times a day. Other therapeutic agents can also be present. Pharmaceutical compositions which provide from about 1 to 50 mg of the active ingredient per unit dose are preferred and are conventionally prepared as tablets, lozenges, capsules, powders, aueous or oily suspensions, syrups, elixirs, and aqueous solutions. Preferred oral compositions are in the form of tablets or capsules and may contain conventional excipients such as binding agents (e.g. syrup, acacia, gelatin, sorbitol, tragecanth, or polyvinylpyrrolidone), fillers (e.g. lactose, sugar, maize-starch, calcium phosphate, sorbitol, or glycine), lubricants (e.g. magnesium stearate, talc, polyethylene glycol or silica), disintegrants (e.g. starch) and wetting agents (e.g. sodium lauryl sulfate). Solutions or suspensions of a Formula I compound with conventional pharmaceutical vehicles are employed for parenteral compositions such as an aqueous solution for intravenous injection or an oily suspension for intramuscular injection. Such compositions having the desired clarity, stability and adaptability for parenteral use are obtained by dissolving from 0.1% to 10% by weight of the active compound in water or a vehicle consisting of a polyhydric aliphatic alcohol such as glycerine, propyleneglycol, and polyethelene glycols or mixtures thereof. The polyethyleneglycols consist of a mixture of non-volatile, usually liquid, polyethyleneglycols which are soluble in both water and organic liquids and which have molecular weights from about 200 to 1500.

DESCRIPTION OF THE SPECIFIC EMBODIMENTS

The compounds which constitute this invention and their methods of preparation will appear more fully from a consideration of the following examples which are given for the purpose of illustration only and are not to be construed as limiting the invention in sphere or scope. All temperatures are understood to be in degrees C. when not specified.

The nuclear magnetic resonance (NMR) spectral characteristics refer to chemical shifts ($\delta$) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), singlet (s), multiplet (m), doublet (d), doublet of doublets (dd), or quarter (q). Abbreviations employed are DMSO-$d_6$ (deuterodimethylsulfoxide), CDCl$_3$ (deuterochloroform), and are otherwise conventional. The infrared (IR) spectral descriptions include only absorption wave numbers (cm$^{-1}$) having functional group identification value. The IR determinations were employed using potassium bromide (KBr) as diluent. The elemental analyses are reported as percent by weight.

Synthesis of Intermediates

A. Intermediates of Formula II

EXAMPLE 1

2-Chloroethyl Acetoacetate

A solution of 75 g (0.403 mole) of 5-(1-hydroxyethylidene)-2,2-dimethyl-1,3-dioxalane-4,6-dione (cf: Y. Oikawa, et al., *J. Org. Chem.*, 43, 2087–2088 (1978)) and 200 mL of 2-chloroethanol was heated at 125° C. for 5 hr. After cooling the dark solution to room temperature, the excess 2-chlorethanol was removed in vacuo and the resulting residue distilled to yield 49.4 g (74%) of product as clear liquid, b.p. 80°–85° C./0.4 mm).

EXAMPLE 2

3-Chloropropyl Acetoacetate

3-Chloropropanol (47.3 g, 0.50 mole) and a catalytic amount of triethylamine at 65° C. were treated dropwise with 42 g (0.50 mole) of diketene. After the addition was complete, the reaction was stirred at 65° C. for an additional hour. Distillation of the residue furnished 72.9 g (82%) of product as a clear liquid, b.p. 78°–85° C. at 150 mm.

Additional Formula II intermediates can be prepared by modifications of the above examples which would be understood by one skilled in the art of organic chemical synthesis.

B. Intermediates of Formula III

EXAMPLE 3

Methyl 2-[(3-Nitrophenyl)methylene]-3-oxobutanoate

A solution of 151 g (1.00 mole) of 3-nitrobenzaldehyde, 116 g (1.00 mole) of methyl acetoacetate, 10 mL of glacial acetic acid, 4 mL of piperidine, and 400 mL of benzene was refluxed 2 hr during which time 21 mL of water was removed via a Dean-Stark trap. The dark yellow solution was cooled to ambient temperature and solidification occurred. Filtration followed by washing with ether afforded 180 g of product as a yellow solid. An additional 23 g product was obtained from the filtrate to yield a total of 203 g (82%) of product, m.p. 145°–146° C. (literature m.p., 158° C.; cf: Meyer, et al., *Arzneim.- Forsch/Drug Research*, 31, 407 (1981)).

EXAMPLE 4

Ethyl 2-[(3-Nitrophenyl)methylene]-3-oxobutanoate

This compound was prepared in molar scale according to the method described above in Example 3 and substituting ethyl acetoacetate for the methyl ester. Recrystallization from ethanol yielded 182 g (69%) of product as a yellow solid, m.p. 103°–106° C. (literature m.p., 110° C.; cf: Ruhemann, *J. Chem. Soc.*, 83, 717 (1903)).

Additional examples of intermediates of Formula III which were prepared using the procedure given above are listed in Table 2.

EXAMPLE 42

4-(2-Methoxyphenyl)-1-piperazinepropanol

The synthesis for this and other V-type intermediates is taken from Wu, et al., *J. Med. Chem.*, 12, 876 (1969). A mixture of 1-(2-methoxyphenyl)piperazine (10.0 g, 52.1 mmole), 3-chloropropanol (4.25 g, 45.0 mmole), micropulverized potassium carbonate (6.21 g, 45 mmole), and 75 mL of acetonitrile was refluxed for 23 hr. After cooling to ambient temperature, 200 mL of water was added and the resulting mixture extracted with methylene chloride. The combined organic portions were washed with water and brine, and then dried over magnesium sulfate. Filtration and removal of volatiles in vacuo yielded 11.7 g of crude alcohol product. Recrystallization from acetonitrile afforded 9.4 g (72%) of product was white solid, m.p. 94°–95° C.

D. Intermediates of Formula VII

EXAMPLE 43

2-Chloroethyl Methyl 1,4-Dihydro-2,6-dimethyl-4-(3-nitrophenyl)-3,5-pyridinedicarboxylate

TABLE 2

Additional Formula III Intermediates

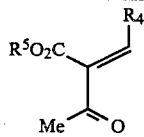

III

| Ex. | $R_4$ | $R_5$ | b.p. (°C./0.1 mm) | m.p. (°C.) |
|---|---|---|---|---|
| 5 | m-nitrophenyl | i-propyl | — | — |
| 6 | m-nitrophenyl | butyl | — | — |
| 7 | m-nitrophenyl | methoxyethyl | — | — |
| 8 | m-nitrophenyl | dimethylaminoethyl | — | — |
| 9 | p-nitrophenyl | ethyl | — | 59.5–61.5 |
| 10 | cyclohexyl | ethyl | 160–170 | — |
| 11 | 1-naphthyl | ethyl | 120–130 | — |
| 12 | 3-indolyl | ethyl | — | 121–122.5 |
| 13 | 2-furanyl | ethyl | 118–120 | — |
| 14 | 2-thienyl | ethyl | 110–120 | — |
| 15 | 3-pyridyl | ethyl | 145–165 | — |
| 16 | 2-bicycloheptenyl | ethyl | 134–140 | — |
| 17 | phenyl | ethyl | 97 | — |
| 18 | m-cyanophenyl | ethyl | 130–160 | — |
| 19 | o-chlorophenyl | ethyl | — | — |
| 20 | m-hydroxy-p-nitrophenyl | ethyl | — | — |
| 21 | o-fluorophenyl | ethyl | 130 | — |
| 22 | m-chlorophenyl | ethyl | 120–123 | — |
| 23 | m-trifluoromethylphenyl | ethyl | 100–110 | — |
| 24 | p-hydroxy-m-nitrophenyl | ethyl | — | — |
| 25 | o-methoxyphenyl | ethyl | — | — |
| 26 | m-methylphenyl | ethyl | 140 | — |
| 27 | p-hydroxy-m-methoxyphenyl | ethyl | — | 110–112 |
| 28 | p-acetomidophenyl | ethyl | — | — |
| 29 | m-methylsulfonyl | ethyl | — | — |
| 30 | m-trifluoromethylsulfonylphenyl | ethyl | — | — |
| 31 | o-chloro-m-nitrophenyl | ethyl | — | — |
| 32 | o-nitrophenyl | methyl | — | — |
| 33 | m-nitrophenyl | methyl | — | 145–146 |
| 34 | m-nitrophenyl | n-propyl | — | — |
| 35 | m-nitrophenyl | 2-chloroethyl | — | 68–76 |
| 36 | m-nitrophenyl | 3-chloropropyl | — | — |
| 37 | 2,3-dichlorophenyl | methyl | — | — |
| 38 | 2,3-dichlorophenyl | methoxyethyl | — | — |
| 39 | 4-benzoxadiazolyl | methyl | — | — |
| 40 | 4-benzthiadiazolyl | ethyl | — | — |
| 41 | 3-(2-methylthiopyridinyl) | methyl | — | — |

C. Intermediates of Formula V

Ammonium acetate (3.85 g, 50.0 mmole) was added to a solution of acetoacetate prepared above in Example 1 (8.25 g, 50.0 mmole) and 50 mL of absolute ethanol, and the refluxed under nitrogen for 1 hr. The cinnamate intermediate product prepared above in Example 3 (12.5 g, 50.0 mmole) was then added and the resulting yellow solution refluxed an additional 12 hr. After cooling to room temperature, the solvent was removed in vacuo and the residue recrystallized from ethanol to yield product as a yellow solid, m.p. 129°–131° C. (Literature m.p., 130° C.; cf: Iwanami, et al., Chem. Pharm. Bull., 27, 1426 (1979)).

EXAMPLE 44

3-Chloropropyl Methyl 1,4-Dihydro-2,6-dimethyl-4-(3-nitrophenyl)-3,5-pyridinedicarboxylate According to the method described above in Example 43 but using the intermediates prepared in Examples 2 and 3, the subject intermediate was prepared in a 99% yield on a 50 mmole scale to yield the product as a yellow solid, m.p. 125°–130° C.

Synthesis of Products

EXAMPLE 45

2-[4-(2-Methoxyphenyl-1-piperazinyl)ethyl]Methyl 1,4-Dihydro-2,6-dimethyl-4-(3-nitrophenyl)-3,5-pyridinedicarboxylate Dihydrochloride Hydrate A solution of the VII intermediate prepared above in Example 43 (1.98 g, 5.00 mmole), 1-(2-methoxyphenyl)-piperazine (1.05 g, 5.5 mmole), triethylamine (0.61 g, 6.04 mmole), and 25 mL of tetrahydrofuran were refluxed for 36 hr under nitrogen. After removal of the volatiles in vacuo, the residue was dissolved in 2-propanol, 50 mL of 10% aqueous HCl (V:V) added and the solution heated on a steam bath for 15 min. After extraction with methylene chloride, the combined organic portions were washed with water and brine, dried over magnesium sulfate, filtered and concentrated in vacuo to yield a brown oil. The oil was crystallized from ethanol:ether to furnish 1.7 g (55%) of product as a light brown solid, m.p. 159°–160° C. (dec.).

Anal. Calcd. for $C_{29}H_{34}N_4O_7.2CHl.0.7H_2O$: C, 54.76; H, 5.93; N, 8.81. Found: C, 54.87; H, 6.21; N, 8.78.

NMR (DMSO-$d_6$): 2.36 (3, s); 2.45 (3, s); 3.45 (10, m); 3.62 (3, s); 3.87 (3, s); 4.55 (2, m); 5.09 (1, s); 7.08 (4, m); 7.70 (2, m); 8.06 (2, m); 8.45 (2, bs); 9.60 (1, bs).

IR (Kbr): 755, 1015, 1100, 1120, 1215, 1350, 1485, 1530, 1650, 1700, 2450, 3360 cm$^{-1}$.

EXAMPLE 46

[2-(4-Phenyl-1-piperazinyl)ethyl]Methyl 1,4-Dihydro-2,6-dimethyl-4-(3-nitrophenyl)-3,5-pyridinedicarboxylate Using methodology similar to that described above in Example 44, a solution of the dihydropyridine intermediate VII and phenylpiperazine were refluxed in acetonitrile using potassium carbonate as the acid acceptor. After hydrochloride formation and crystallization from acetonitrile-isopropyl ether, the product was obtained in 15% yield as a yellow solid, m.p. 201°–204° C.

Anal. Calcd. for $C_{28}H_{32}N_4O_6.HCl$: C, 60.37; H, 5.97; N, 10.06. Found: C, 60.48; H, 6.11; N, 10.30.

NMR (DMSO-$d_6$): 2.32 (3, s); 2.40 (3, s); 3.21 (6, m); 3.44 (4, m); 3.60 (3, s); 4.48 (2, m); 5.04 (1, s); 6.92 (3, m); 7.28 (2, m); 7.64 (2, m); 8.01 (2, m); 9.40 (1, bs); 11.65 (1, bs).

IR (KBr): 695, 755, 1100, 1120, 1215, 1350, 1480, 1525, 1670, 1700, 2430, 3280 cm$^{-1}$.

EXAMPLE 47

[3-[4-(2-Methoxyphenyl)-1-piperazinyl]propyl]Methyl 1,4-Dihydro-2,6-dimethyl-4-(3-nitrophenyl)-3,5-pyridinedicarboxylate Hydrate A solution of the dihydropyridine intermediate VII prepared above in Example 44 (8.65 g, 20 mmole), 1-(2-methoxyphenyl)piperazine (4.1 g, 20 mmole), triethylamine (6 g), and a catalytic amount of potassium iodide in 50 mL of acetonitrile was refluxed for 48 hr. After removal of volatiles in vacuo, the residue was triturated in acetonitrile to furnish 3.5 g (17%) of product as a yellow solid, m.p. 70°–75° C.

Anal. Cacld. for $C_{30}H_{36}N_4O_7.0.5H_2O$: C, 62.81; H, 6.50; N, 9.77. Found: C, 62.50; H, 6.41; N, 9.43.

NMR (DMSO-$d_6$): 1.72 (2, m); 2.30 (6, s); 2.40 (6, m); 2.92 (4, m); 3.56 (3, s); 3.77 (3, s); 4.02 (2, m); 5.02 (1, s); 6.87 (4, m); 7.59 (2, m); 8.00 (2, m); 9.01 (1, bs).

IR (KBr): 750, 1100, 1120, 1215, 1240, 1350, 1500, 1530, 1685, 1700, 3400 cm$^{-1}$.

EXAMPLE 48

Methyl 1,4-Dihydro-5-[[[2-(4-(2-methoxyphenyl)-1-piperazinyl)]ethyl]amino]carbonyl-2,6-dimethyl-4-(3-nitrophenyl)-3-pyridinecarboxylate Diketene (1.85 g, 22.0 mmole) was slowly added dropwise to a 0° C. solution of 1-(2-aminoethyl)-4-(2-methoxyphenyl)piperazine (4.7 g, 22 mmole; cf: Mull, et al., J. Med. Pharm. Chem., 5, 944 (1962) for preparation) in 20 mL of absolute ethanol. After the addition was complete, the solution was allowed to warm to room temperature and was stirred 30 minutes. Concentration in vacuo gave 5.5 g of the crude acetoacidamide intermediate as a clear oil which was used without further purification.

The Knovenagel condensation was achieved by refluxing the solution of 3-nitrobenzaldehyde (2.25 g, 15 mmole), the acetoacidamide intermediate, 5 drops of glacial acetic acid, and 3 drops of piperidine in 25 mL of benzene for several hours. After work up and flash chromatograophy (5% methanol:chloroform) 4.35 (44%) of product was obtained as a yellow oil.

A portion of this yellow oil (3.5 g, 7.7 mmole) methyl 3-aminocrotonate (3.9 g, 7.8 mmole) and 40 mL of 2-propanol was refluxed overnight (18 hr). Concentration in vacuo gave 3.5 g of a yellow gum. Flash chromatography (2% methanol:chloroform; 3% methanol:chloroform; and then 4% methanol:chloroform) afforded 0.73 g (17%) of product as a yellow foam, m.p. 83°–88° C.

Anal. Cacld. for $C_{29}H_{35}N_5O_6.0.2CHCl_3$: C, 61.15; H, 6.19; N, 12.21. Found: C, 61.08; H, 6.18; N, 11.93.

NMR (CDCl$_3$): 2.30 (6, s); 2.54 (6, m); 3.01 (4, m); 3.32 (2, m); 3.63 (3, s); 3.85 (3, s); 4.96 (1, s); 6.16 (1, bs); 6.26 (1, bs); 6.92 (4, m); 7.38 (1, m); 7.68 (1, m); 8.05 (2, m).

IR (KBr): 750, 1110, 1240, 1350, 1500, 1530, 1625, 1660 cm$^{-1}$.

EXAMPLE 49

Methyl 1,4-Dihydro-5-[[[3-[4-(2-methoxyphenyl)-1-piperazinyl]propyl]amino]carbonyl]-2,6-dimethyl-4-(3-nitrophenyl)-3-pyridinecarboxylate This compound was prepared in similar fashion to Example 48 but using a starting aminopropylpiperazine described in Wu, et al., *J. Med. Chem.*, 12, 876 (1969). The desired product was isolated as a yellow foam, m.p. 70°–80° C.

Anal. calcd. for $C_{30}H_{37}N_5O_6.0.4CHCl_3$: C, 59.72; H, 6.17; N, 11.45. Found: C, 59.54; H, 6.17; N, 11.38.

NMR (CDCl$_3$): 1.65 (2, m); 2.17 (3, s); 2.31 (3, s); 2.52 (6, m); 3.00 (4, m); 3.38 (2, m); 3.53 (3, s); 3.85 (3, s); 4.99 (1, s); 5.90 (1, bs); 6.89 (5, m); 7.52 (2, m); 8.03 (2, m.).

IR (KBr): 750, 1115, 1230, 1240, 1350, 1500, 1530, 1625, and 1680 cm$^{-1}$.

EXAMPLE 50 bis-[3-[4-(2-Methoxyphenyl)-1-piperazinyl]propyl]1,4-Dihydro-2,6-dimethyl-4-(3-nitrophenyl)-3,5-pyridinedicarboxylate Dihydrochloride To a melt of the piperazine intermediate V, prepared above in Example 42 (5.00 g, 20.0 mmole) in a 105° C. oil bath was slowly added diketene (1.68 g, 20.0 mmole). After the addition was complete, 50 mL of absolute ethanol, ammonium acetate (1.20 g, 16 mmole), and 3-nitrobenzaldehyde (1.58 g, 10.4 mmole) were added, and the resulting solution refluxed for 17 hr. After cooling to room temperature, the reaction was concentrated in vacuo to yield 8.5 g of a dark yellow oil. The oil was taken up in methylene chloride and washed with two portions of 10% aqueous HCl (V:V) and the organic layer concentrated to yield a yellow solid. Recrystallization from ethanol-ethyl ether furnished 2.95 g (35%) of product as a yellow solid, m.p. 155°–175° C. (dec.).

Anal. Calcd. for $C_{43}H_{54}N_6O_8.2HCl.0.5H_2O$: C, 59.72; H, 6.64; N, 9.72; H$_2$O, 1.04. Found: C, 59.67; H, 6.90; N, 9.54; H$_2$O, 1.04.

NMR (DMSO-d$_6$): 2.18 (4, m); 2.38 (6, s); 3.18 (12, m); 3.44 (8, m); 3.79 (6, s); 4.08 (4, m); 5.00 (1, s); 6.93 (8, m); 7.70 (2, m); 8.02 (2, m); 9.46 (1, bs).

IR (KBr): 750, 1120, 1215, 1250, 1350, 1515, 1550, 1665, 1710, 2640, and 3400 cm$^{-1}$.

EXAMPLE 51

4-[4-[(2-Methoxyphenyl)-1-piperazinyl]butyl]Methyl 1,4-Dihydro-2,6-dimethyl-4-(3-nitrophenyl)-3,5-pyridinedicarboxylate Dihydrochloride Diketene (4.6 g, 0.055 mole) was added dropwise to 4-(2-methoxyphenyl)-1-piperazinebutanol (13.2 g, 0.05 mole) (Brit. No. 803,403, Oct. 22, 1958) at 100°. The melt was heated for 20 min at 100°. The melt was dissolved in 200 mL ethanol and ammonium acetate (3.5 g, 0.05 mole) added. The solution was heated at reflux for 2 hr. Methyl m-nitro-2-acetylcinnamate (8.4 g, 0.05 mole) was added and refluxing was continued for 17 hr. The solution was concentrated in vacuo. The residue was purified by flash chromatography (2% MeOH in CHCl$_3$ on silica gel). The product was converted to the hydrochloride with ethanolic HCl to give 1.55 g (4.7%) of product, m.p. 110–130.

Anal. Calcd. for $C_{31}H_{38}N_4O_7.2HCl$: C, 57.14; H, 6.19; N, 8.60. Found C, 57.35; H, 6.39; N, 8.51.

Additional examples of products of the instant invention are given in Table 3. These additional products are synthesized using the procedures described above in Examples 45–51.

TABLE 3

Additional Formula I Products

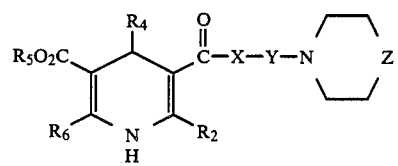

| Ex. No. | R$_2$ | R$_4$ | R$_5$ | R$_6$ | X | Y | Z |
|---|---|---|---|---|---|---|---|
| 52 | Me | 3-NO$_2$Ph | Me | Me | O | —(CH$_2$)$_3$— | 2-pyrimidinyl |
| 53 | Me | 3-NO$_2$Ph | R$_3^{(a)}$ | Me | O | —(CH$_2$)$_3$— | 2-pyrimidinyl |
| 54 | Me | 3-NO$_2$Ph | Me | Me | O | —(CH$_2$)$_3$— | 2-(3-CN—pyridyl) |
| 55 | Me | 3-NO$_2$Ph | Me | Me | O | —(CH$_3$)$_3$— | 3-CF$_3$Ph |
| 56 | Me | 3-NO$_2$Ph | Et | Me | O | —(CH$_2$)$_3$— | 2-MeOPh |
| 57 | Me | 3-NO$_2$Ph | Me | M3 | O | —[CH$_2$]$_3$NH[CH$_2$]$_3$— | 2-MeOPh |
| 58 | Me | 3-NO$_2$Ph | Me | Me | O | —[CH$_2$]$_2$O[CH$_2$]$_2$— | 2-MeOPh |
| 59 | Me | 3-NO$_2$Ph | R$_3^{(a)}$ | Me | O | —[CH$_2$]$_2$O[CH$_2$]$_2$— | 2-MeOPh |
| 60 | Me | 3-NO$_2$Ph | MeOCH$_2$CH$_2$— | Me | O | —(CH$_2$)$_3$— | 2-MeOPh |
| 61 | Me | 2-NO$_2$Ph | Me | Me | O | —(CH$_2$)$_3$— | 2-MeOPh |
| 62 | Me | 3-NO$_2$Ph | Me | Me | O | —(CH$_2$)$_3$— | 3-ClPh |
| 63 | Me | 3-NO$_2$Ph | Me | Me | O | —(CH$_2$)$_3$— | 4-FPh |
| 64 | Me | 3-NO$_2$Ph | R$_3^{(a)}$ | Me | O | —(CH$_2$)$_3$— | 4-FPh |
| 65 | Me | 3-NO$_2$Ph | Me | Me | O | —(CH$_2$)$_3$— | 2-CF$_3$Ph |
| 66 | Me | 3-NO$_2$Ph | Me | Me | O | —(CH$_2$)$_3$— | 2-MePh |
| 67 | Me | 3-NO$_2$Ph | R$_3^{(a)}$ | Me | O | —(CH$_2$)$_3$— | 2-MePh |
| 68 | Me | 3-NO$_2$Ph | ME$_2$NCH$_2$CH$_2$ | Me | O | —(CH$_2$)$_3$— | 2-MeOPh |
| 69 | CH$_2$OH | 3-NO$_2$Ph | Me | Me | O | —(CH$_2$)$_2$— | 2-MePh |
| 70 | CH$_2$OMe | 2,3-ClPh | MeOCH$_2$CH$_2$ | Me | O | —(CH$_2$)$_3$— | 3-ClPh |
| 71 | CH$_2$NMe$_2$ | 2-NO$_2$Ph | Et | Me | O | —(CH$_2$)$_4$— | 3-MeOPh |
| 72 | Me | 4-C$_6$H$_3$N$_2$O | Me | Me | O | —(CH$_3$)$_3$— | 2-MeOPh |
| 73 | Et | 4-C$_6$H$_3$N$_2$S | Me | Me | O | —(CH$_2$)$_3$— | 2-MeOPh |
| 74 | Me | 3-CNPh | Et | MeOCH$_2$ | O | —(CH$_2$)$_3$— | 3-CF$_3$Ph |
| 75 | MeOCH | 3-C$_6$H$_6$NS | Me | Et | O | —(CH$_2$)$_3$— | 2-MeOPh |

TABLE 3-continued

Additional Formula I Products $$R_5O_2C-C(R_4)=C-C(=O)-X-Y-N\underset{\underset{\diagdown}{\diagup}}{\diagdown}Z$$
(structure I: dihydropyridine with $R_6$, NH, $R_2$ ring and piperazinyl group)

| Ex. No. | $R_2$ | $R_4$ | $R_5$ | $R_6$ | X | Y | Z |
|---|---|---|---|---|---|---|---|
| 76 | Me$_2$NCH | 2-NO$_2$ | Me | Me | O | —(CH$_2$)$_4$— | 3-FPh |

[a] $R_3$ = Y—N  N—Z; i.e. compounds where $R_5$ = $R_3$ represent the symmetrical 3,5-dicarboxylate dihydropyridine products.

The physical properties, where available, of the products of the examples listed in Table 3 are given in Table 4 which follows.

lar properties. For instance, they possess calcium entry and alpha-adrenergic blockade as well as antihypertensive activity. The significance of such findings has al-

TABLE 4

Physical Properties - Formula I Products

| Ex. | Name | m.p. (°C.) | | Anal Calcd | Found |
|---|---|---|---|---|---|
| 52 | [3-[1-(2-Pyrimidinyl)-4-piperazinyl]propyl] Methyl 1,4-dihydro-2,6-dimethyl-4-(3-nitrophenyl)-3,5-pyridinedicarboxylate Hydrochloride Acetonitrile Solvate | 97–110 | C, H, N, | 57.56 5.93 15.90 | 57.28 6.00 15.95 |
| 53 | Bis[3-[1-(2-Pyrimidinyl)-4-piperazinyl]propyl] 1,4-Dihydro-2,6-dimethyl-4-(3-nitrophenyl)-3,5-pyridinedicarboxylate Hydrochloride | 92–105 | C, H, N, | 58.22 6.21 18.35 | 57.93 6.32 18.43 |
| 54 | [3-[4-(3-Cyano-2-pyridinyl)-1-piperazinyl]propyl] Methyl 1,4-Dihydro-2,6-dimethyl-4-(3-nitrophenyl)-3,5-pyridinedicarboxylate Hydrochloride | 230–232 | C, H, N, | 58.34 5.57 14.06 | 58.36 5.66 14.08 |
| 55 | [3-[4-[3-(Trifluoromethyl)phenyl]-1-piperazinyl]propyl] Methyl 1,4-Dihydro-2,6-dimethyl-4-(3-nitrophenyl)-3,5-pyridinedicarboxylate Hydrochloride | 215–217 | C, H, N, | 56.38 5.36 8.77 | 55.99 5.53 8.88 |
| 56 | Ethyl [3-[4-(2-Methoxyphenyl)-1-piperazinyl]propyl] 1,4-Dihydro-2,6-dimethyl-4-(3-nitrophenyl)-3,5-pyridinedicarboxylate Hydrochloride Hydrate | Indistinct | C, H, N, | 60.09 6.43 9.04 | 59.94 6.42 9.21 |
| 57 | [3-[[3-[4-(2-Methoxyphenyl))-1-piperazinyl]]propyl]amino]propyl] Methyl 1,4-Dihydro-2,6-dimethyl-4-(3-nitrophenyl)-3,5-pyridinedicarboxylate Dihydrochloride Hydrate | Indistinct | C, H, N, | 55.95 6.87 9.89 | 55.90 6.79 9.74 |
| 58 | [2-[2-[4-(2-Methoxyphenyl)-1-piperazinyl]ethoxy]ethyl] Methyl 1,4-Dihydro-2,6-dimethyl-4-(3-nitrophenyl)-3,5-pyridinedicarboxylate Hydrochloride Hydrate | 103–113 | C, H, N, | 58.00 6.31 8.73 | 57.65 6.21 8.55 |
| 59 | BIS[2-[2-[4-(2-Methoxyphenyl)-1-piperazinyl]ethoxy]ethyl] 1,4-Dihydro-2,6-dimethyl-4-(3-nitrophenyl)-3,5-pyridinedicarboxylate Tetrahydrochloride Monohydrate | 178–180 | C, H, N, | 53.68 6.41 8.35 | 53.42 6.70 8.13 |
| 60 | (2-Methoxyethyl) [3-[4-(2-Methoxyphenyl)-1-piperazinyl]propyl] 1,4-dihydro-2,6-dimethyl-4-(3-nitrophenyl)-3,5-pyridinedicarboxylate Monohydrate | 212–216 | C, H, N, | 59.58 6.41 8.68 | 59.58 6.48 8.87 |
| 61 | [3-[4-(2-Methoxyphenyl)-1-piperazinyl]propyl] Methyl 1,4-Dihydro-2,6-dimethyl-4-(2-nitrophenyl)-3,5-pyridinedicarboxylate Monohydrochloride Hemihydrate | 120–130 | C, H, N, | 59.06 6.28 9.18 | 59.19 6.21 9.12 |
| 62 | [3-[4-(3-Chlorophenyl)-1-piperazinyl]propyl] Methyl 1,4-Dihydro-2,6-dimethyl-4-(3-nitrophenyl)-3,5-pyridinedicarboxylate Monohydrochloride | 97–102 | C, H, N, | 57.52 5.66 9.25 | 57.90 5.71 9.42 |
| 63 | [3-[4-(4-Fluorophenyl)-1-piperazinyl]propyl] Methyl Dihydro-2,6-dimethyl-4-(3-nitrophenyl)-3,5-pyridinedicarboxylate | 126–128 | C, H, N, | 60.03 6.02 10.14 | 62.92 6.09 9.88 |
| 64 | BIS[3-[4-(4-Fluorophenyl)piperazinyl]propyl] 1,4-Dihydro-2,6-dimethyl-4-(3-nitrophenyl)-3,5-pyridinedicarboxylate | 175–176 | C, H, N, | 64.89 6.38 11.07 | 64.81 6.47 11.05 |
| 65 | Methyl [3-[4-(2-Trifluoromethyl)phenyl]-1-piperazinyl]propyl] 1,4-Dihydro-2,6-dimethyl-4-(3-nitrophenyl)-3,5-pyridinedicarboxylate | 151–153 | C, H, N, | 59.80 5.52 9.30 | 59.90 5.62 9.05 |
| 66 | Methyl [3-[4-(2-Methylphenyl)-1-piperazinyl]propyl] 1,4-Dihydro-2,6-dimethyl-4-(3-nitrophenyl)-3,5-pyridinedicarboxylate | 120–124 | C, H, N, | 65.68 6.61 10.21 | 65.75 6.74 9.85 |
| 67 | BIS[3-[4-(2-Methylphenyl)-1-piperazinyl]propyl] 1,4-Dihydro-2,6-dimethyl-4-(3-nitrophenyl)-3,5-pyridinedicarboxylate | 136–138 | C, H, N, | 68.78 7.25 11.19 | 68.61 7.42 11.30 |
| 68 | [2-(N,N—Dimethylamino)ethyl] [3-[4-(2-Methoxyphenyl)-1-piperazinyl]propyl] 1,4-Dihydro-2,6-dimethyl-4-(3-nitrophenyl)-3,5-pyridinedicarboxylate Trihydrochloride | 212–213 | C, H, N, | 54.21 6.34 9.58 | 54.38 6.46 9.96 |

Further Detailed Description of the Invention

Some additional compounds similar to those defined hereinabove by Formula I also have useful cardiovascular ready been adequately discussed supra for the Formula I compounds. The additional compounds are synthesized as illustrated in Examples 77 and 78 hereinbelow and are embodied in Formula I' along with the compounds of Formula I.

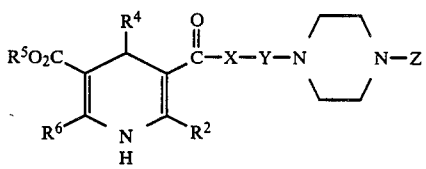

For compounds of Formula I', $R^2$, $R^4$, $R^5$, $R^6$, X and Z are as previously defined for compounds of Formula I. The definition for Y, however, is expanded in Formula I' to include alkylene chains of from 2 to 5 carbon atoms and alkylene chains containing a sulfur atom in the chain. The scope of the instant invention is hereby expanded to include all compounds defined by Formula XXI (shown below) which incorporates the compounds of I and I'. The present subject matter now comprises compounds of Formula XXI

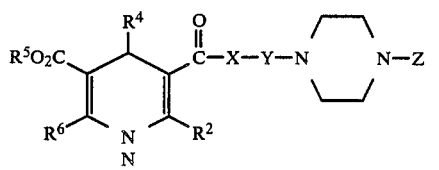

or a pharmaceutically acceptable acid addition salt and/or solvate thereof wherein the symbols $R^2$, $R^4$, $R^5$, $R^6$, X, Y and Z have the following meanings. $R^2$ and $R^6$ are independently selected from lower alkyl, hydroxyalkyl, alkoxyalkyl, alkylaminoalkyl, or dialkylaminoalkyl and may be the same or different. Lower alkyl means $C_1$–$C_4$; alkoxyalkyl refers to a $C_1$–$C_4$ alkylene chain and a $C_1$–$C_4$ alkyl group connected by an oxygen atom; similarly, alkylaminoalkyl and dialkylaminoalkyl refer to lower alkyl groups and a $C_{1-4}$ alkylene chain connected by a secondary (—NH—) or a tertiary

amino group. $R^4$ is cycloalkyl of 5 to 7 carbon atoms, bicycloalkenyl of 7 to 9 carbon atoms, hetaryl, such as furanyl, indolyl, methylthiopyridyl, thienyl, benzoxadiazolyl, benzothiadiazolyl, and the like; aryl meaning phenyl, naphthyl, or substituted phenyl, with a substituent comprising acetamino, lower alkyl, lower alkoxy, cyano, halogen, hydroxyl, nitro, trifluoromethyl, trifluoromethylsulfonyl, and methylsulfonyl and the like. $R^5$ is $R^2$ or

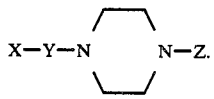

X is O or NH. Y is an alkylene chain containing 2 to 5 carbon atoms, or an alkyleneoxyalkylene, alkyleneaminoalkylene, or alkylenethioalkylene chain. By alkyleneoxyalkylene is meant two $C_2$ to $C_5$ alkylene chains connected by an oxygen atom. Similarly, alkyleneaminoalkylene and alkylenethioalkylene denote $C_2$ to $C_5$ alkylene chains connected by NH and S, respectively. Z is phenyl, pyridyl, or pyrimidinyl, either unsubstituted or substituted with one or more substituent groups selected from among lower alkyl, lower alkoxy, cyano, halo, and trifluoromethyl.

The additional compounds embodied in Formula I' can be prepared by adapting the synthetic processes outlined as Schemes 1–3. Specifically, the compounds of Formula I' are obtained by use of the methods for Formula I compounds previously set forth or by obvious modification of these procedures. This is illustrated by the following examples.

EXAMPLE 77

[2-[[2-[4-(2-Methoxyphenyl)-1-piperazinyl]ethyl]thio]ethyl]Methyl 1,4-Dihydro-2,6-dimethyl-4-(3-nitrophenyl)-3,5-pyridine Dicarboxylate Diketene (8.4 g, 100 mmole) was added dropwise to 2,2-thiodiethanol (12.2 g, 100 mmole) at 80° containing a catalytic amount of triethylamine. The mixture was heated for 15 minutes at 80°. The mixture was dissolved in 200 mL ethanol and ammonium acetate (7.7 g, 100 mmole) was added. The solution was then heated at reflux for an hour. Methyl 2-[(3-nitrophenyl)methylene]-3-oxobutanoate (Ex. 3, 24.9 g, 100 mmole) was added and refluxing continued for 18 hr. The solution was concentrated in vacuo and the residue purified by flash chromatography (2% MeOH in methylene chloride on silica gel) gave 5 g (21.8%) of a synthetic intermediate compound whose structure is a modification of compound VII (Cl replaced by OH).

A solution of this intermediate alkylenethioalkanol compound (4.0 g, 9.2 mmole) and thionyl chloride (1.1 g, 9.2 mmole) in 100 mL chloroform was heated at reflux for about 1.25 hr. The solution was concentrated in vacuo. The residue was dissolved in 300 mL acetonitrile and combined with o-methoxyphenylpiperazine (3.5 g, 18 mmole); micropulverized potassium carbonate (2.5 g, 18 mmole); and a crystal of sodium iodide. The mixture was heated at reflux for four days and concentrated in vacuo. The residue was purified by flash chromatography (0.5% methanol and 1:4 ethyl acetate-methylene chloride on silica gel) to give 2.2 g (39.3%) of product, m.p. 52°–63°.

Anal. Calcd. for $C_{31}H_{38}N_4O_7S$: C, 60.98; H, 6.27; N, 9.17. Found: C, 60.61; H, 6.24; N, 9.46.

EXAMPLE 78

[5-[4-(2-Methoxyphenyl)-1-piperazinyl]pentyl]Methyl 1,4-Dihydro-2,6-dimethyl-4-(3-nitrophenyl)-3,5-pyridinedicarboxylate Dichloromethane Solvate Diketene (3.0 g, 36 mmole) was added slowly to a melt of 1-(5-hydroxypentyl)-4-(2-methoxyphenyl)piperazine (10.0 g, 36 mmole; prepared according to Brit. Patent No. 803,403, Oct. 22, 1958) at 85°. After the addition was complete, 100 mL abs. ethanol and ammonium acetate (2.8 g, 36 mmole) were added. After refluxing for 2 hr, methyl 2-[(3-nitrophenyl)methylene]-3-oxobutanoate (9.0 g, 36 mmole; prepared in Example 3) was added and reflux was continued for 17 hr. The solution was concentrated in vacuo. The residue was purified by flash chromatography (1.5% methanol and methylene chloride) to give 5.2 g (23.7%) of product, m.p. 52°–62°.

Anal. Calcd. for $C_{32}H_{40}N_4O_7 \cdot 0.2CH_2Cl_2$: C, 63.44; H, 6.68; N, 9.19. Found: C, 63.59; H, 6.73; N, 9.32.

What is claimed is:
1. A compound of Formula XXI'

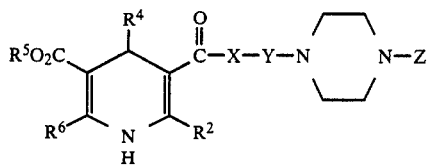

and the pharmaceutically acceptable acid addition salts thereof wherein $R^2$ and $R^6$ are independently selected from lower alkyl, hydroxy-lower-alkyl, lower-alkoxy-lower-alkyl, lower-alkylamino-lower-alkyl, or di-lower alkylamino-lower-alkyl;

$R^4$ is cycloalkyl of 5-7 carbons, bicycloalkenyl of 7-9 carbon atoms, furanyl, indolyl, methylthiopyridyl, thienyl, benzoxadiazolyl, and benzothiadiazolyl; phenyl, naphthyl, or substituted phenyl, with a substitutent selected from the group consisting of acetamino, lower alkyl, lower alkoxy, cyano, halogen, hydroxyl, nitro, trifluoromethyl, trifluoromethylsulfonyl, and methylsulfonyl;

$R^5$ is $R^2$ or

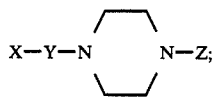

X is NH;

Y is a $C_2$ to $C_5$ alkylene chain, alkyleneoxyalkylene, alkylenethioalkylene, or alkyleneaminoalkylene chain wherein each alkylene moiety having 2-5 carbon atoms; and Z is phenyl, pyridinyl, or pyrimidinyl, either unsubstituted or substituted with a group selected from among lower alkyl, lower alkoxy, cyano, halo, and trifluoromethyl.

2. The compound of claim 1 wherein $R^2$ and $R^6$ are lower alkyl, $R^4$ is nitrophenyl, $R^5$ is lower alkyl or

X—Y—N⟨ ⟩N—Z,

X is NH, Y is a $C_2$–$C_4$ alkylene chain or an alkyleneoxyalkylene chain wherein each alkylene moiety having 2-5 carbon atoms, and Z is phenyl substituted by lower alkyl, lower alkoxy, cyano, halo or trifluoromethyl.

3. The compound of claim 2 which is methyl 1,4-dihydro-5-[[[3-[4-(2-methoxyphenyl)-1-piperazinyl]propyl]amino]carbonyl]-2,6-dimethyl-4-(3-nitrophenyl)-3-pyridinecarboxylate.

4. The compound of claim 2 which is methyl 1,4-dihyro-5-[[[2-[4-(2-methoxyphenyl)-1-piperazinyl]ethyl]amino]carbonyl]-2,6-dimethyl-4-(3-nitrophenyl)-3-pyridinecarboxylate.

5. The method of exerting a vasodilating effect in a mammalian host which comprises administering to a mammal having a condition in which therapeutic benefit is derived from vasodilation, a non-toxic effective vasodilating dose of a compound as claimed in claim 1.

6. The antihypertensive method which comprises administering to a mammalian host having hypertension a non-toxic antihypertensive effective dose of a compound claimed in claim 1.

7. The anti-ischemia method which comprises administering to a mammalian host, subject to ischemic attack, a non-toxic antiischemia effective dose of a compound claimed in claim 1.

8. The method of inihibiting blood platelet function which comprises administering to a mammal having a condition in which therapeutic benefit is derived from blood platelet function inhibition, a non-toxic effective blood platelet function inhibitory dose of a compound as claimed in claim 1.

9. A pharmaceutical composition for the treatment of cardiovascular disease consisting of angina, hypertension, or ischemia comprising from 5 to 50 mg of a compound claimed in claim 1 in combination with a pharmaceutically acceptable, non-toxic inert carrier.

* * * * *